United States Patent
Coupard et al.

(10) Patent No.: US 9,132,414 B2
(45) Date of Patent: Sep. 15, 2015

(54) PROCESS FOR DEHYDRATION AND ISOMERIZATION OF C4 ALCOHOLS USING AN AMORPHOUS SOLID WITH SUITABLE POROSITY

(75) Inventors: Vincent Coupard, Villeurbanne (FR); Sylvie Maury, Charly (FR); Karine Surla, Saint Cyr sur le Rhone (FR)

(73) Assignee: IFP ENERGIES NOUVELLES, Rueil-Malmaison Cedex (FR)

( * ) Notice: Subject to any disclaimer, the term of this patent is extended or adjusted under 35 U.S.C. 154(b) by 330 days.

(21) Appl. No.: 13/703,107

(22) PCT Filed: May 27, 2011

(86) PCT No.: PCT/FR2011/000316
§ 371 (c)(1),
(2), (4) Date: Feb. 4, 2013

(87) PCT Pub. No.: WO2011/154621
PCT Pub. Date: Dec. 15, 2011

(65) Prior Publication Data
US 2013/0137908 A1    May 30, 2013

(30) Foreign Application Priority Data
Jun. 11, 2010 (FR) .................................... 10 02469

(51) Int. Cl.
| | |
|---|---|
| *B01J 21/04* | (2006.01) |
| *C07C 1/24* | (2006.01) |
| *C07C 5/27* | (2006.01) |
| *C07C 11/08* | (2006.01) |
| *C07C 11/09* | (2006.01) |

(52) U.S. Cl.
CPC . *B01J 21/04* (2013.01); *C07C 1/24* (2013.01); *C07C 5/2772* (2013.01); *C07C 5/2775* (2013.01); *C07C 11/08* (2013.01); *C07C 11/09* (2013.01); *C07C 2521/04* (2013.01); *C07C 2521/06* (2013.01); *C07C 2523/04* (2013.01); *C07C 2523/06* (2013.01); *C07C 2523/20* (2013.01); *C07C 2523/22* (2013.01); *C07C 2523/26* (2013.01); *C07C 2523/28* (2013.01); *C07C 2523/30* (2013.01)

(58) Field of Classification Search
None
See application file for complete search history.

(56) References Cited

U.S. PATENT DOCUMENTS

| | | | | |
|---|---|---|---|---|
| 2,499,675 | A * | 3/1950 | Owen | 502/320 |
| 4,404,417 | A |  9/1983 | Adams et al. | |
| 4,514,511 | A * | 4/1985 | Jacques et al. | 502/8 |
| 5,545,793 | A |  8/1996 | Travers et al. | |

FOREIGN PATENT DOCUMENTS

| | | |
|---|---|---|
| EP | 0071199 A1 | 2/1983 |
| EP | 0659719 A1 | 6/1995 |
| FR | 2484400 A1 | 12/1981 |

OTHER PUBLICATIONS

Macho, Kralik, Jurecekova, Hudec, and Jurecek. Dehydration of C4 alkanols conjugated with a positional and skeletal isomerisation of formed C4 alkenes, Applied Catalysis A: General 214 (2001) 251-257.*
Macho, Kralik, Jurecek, Jurecekova, and Balazova. Skeletal isomerisation of n-butenes present in C4 pyrolysis residue fraction, Applied Catalysis A: General 203 (2000) 5-14.*
Bartholomew and Farrauto. Fundamentals of Industrial Catalytic Processes, Chapter 3: Catalyst Characterization and Selection, 2nd Edition, 2005.*
International Search Report for PCT/FR2011/000316 mailed on Jul. 26, 2011.
English Translation of Abstract for FR2484400 (A1) dated Dec. 18, 1981.
English Translation of Abstract for EP0659719 (A1) dated Jun. 28, 1995.
Written Opinion of the ISA mailed on Jul. 26, 2011.
Vendelin Macho et al. "Dehydration of C4 alkanols conjugated with a positional and skeletal isomerisation of the formed C4 alkenes" Applied Catalysis A: General 214 (2001) pp. 251-257.
Dazhi Zhang et al. "One-step dehydration and isomerisation of the n-butanol to iso-butene over zeolite catalysts" Chem. Commun., (2010) 46 pp. 4088-4090.
M. A. Makarova et al. "Dehydration of n-Butanol on Zeolite H-ZSM-5 and Amorphous Aluminosilicate: Detailed Mechanistic Study and the Effect of Pore Confinement" Journal of Catalysis 149 (1994) pp. 36-51.
P. Berteau, et al. "Role of the acid-base properties of Aluminas, modified y-Alumina, and Silica-Alumina in 1-Butanol Dehydration" Applied Catalysis, 31 (1987) pp. 361-383.
R. Mann "Catalyst deactivation by coke deposition: Approaches based on interactions of coke laydown with pore structure" Catalysis Today 37 (1997) pp. 331-349.
Ryoji Takahashi et al. "Effect of diffusion in catalytic dehydration of alcohol over silica-alumina with continuous macropores" Journal of Catalysis 229 (2005) pp. 24-29.

* cited by examiner

*Primary Examiner* — In Suk Bullock
*Assistant Examiner* — Ali Z Fadhel
(74) *Attorney, Agent, or Firm* — Millen, White, Zelano & Branigan, P.C.

(57) ABSTRACT

The present invention relates to a method of producing C4 olefins, from a feed of C4 monohydric alcohol, in which a reaction of dehydration of the monohydric alcohol to at least one olefin, and a reaction of skeletal isomerization of at least one of the olefins produced in one and the same reaction vessel, are carried out in the presence of an alumina-based catalyst with adapted porosity.

14 Claims, No Drawings

PROCESS FOR DEHYDRATION AND ISOMERIZATION OF C4 ALCOHOLS USING AN AMORPHOUS SOLID WITH SUITABLE POROSITY

TECHNICAL FIELD OF THE INVENTION

The present invention relates to an improved method of producing C4 alkenes or butenes from a feed of C4 monohydric alcohols or butanol. The butanol feed used is of biological or chemical origin. This method employs an amorphous catalyst having a porosity oriented towards a distribution with a high level of open macroporosity.

By "open macroporosity" is meant the pore spaces connected to the porous network and accessible to the wetting fluids used in the methods of measuring porosity such as mercury porosimetry. This macroporosity is therefore detectable by this method, described below.

The alkenes obtained, and in particular isobutene and 1-butene, are of considerable interest in the field of the petrochemical industry and organic synthesis, isobutene being a key compound in the chemistry of the significant intermediates.

PRIOR ART

The dehydration of C4 monohydric alcohols has been investigated for many years, mainly as a route of synthesis or purification of isobutene. Catalysts based on mineral acid, $FeCl_2$ salt, metal oxides such as alumina or zeolite have been used in this application. The article by Adkins et al., JACS April 1925, Vol. 47, pp. 1163-1167, where it is noted that alumina, after activation in air, is effective for a short time in the dehydration of many alcohols, may be mentioned. The authors note that only activation in air can make alumina active in this application.

The article by Makarova et al. (Journal of Catalysis, 149, 36-51 (1994)), which teaches that zeolites (ZSM-5) and silica-alumina are also active in dehydration, may also be mentioned. In the conclusion of their study, the authors note the absence of diffusion problems in these two systems, similar activity being observed for systems employing solids having pore sizes varying from 0.5 to 5 nm.

Finally the works of P. Berteau et al. described in Applied Catalysis, Volume 31, Issue 2, 1987, pp. 391-383 which aim to modulate the acidity of alumina by adding a promoter ($F^-$, $Na^+$), observing the effect on the dehydration reaction, may be mentioned. Coking is reported for these solids, but no notable deactivation is mentioned for the 35 to 70 hours of the test. It is noted that the addition of Nat causes a notable decrease in the activity of the alumina catalyst.

Patent application EP-B1-0 659 719 describes a method of isomerization of the skeleton and of the position of the double bond of C4 olefins using an alumina-based material, which had undergone a particular forming process in the presence of a silica-based precursor. This reaction is used in a process in which water is co-introduced with the olefinic feed in order to limit parasitic reactions. The tests given as examples show the performance obtained after 1 h of operation, which is a relatively short time and may suggest that the stability of the catalyst over time can still be improved. As the reaction of skeletal isomerization is always accompanied by undesirable secondary reactions, a loss of activity of the catalyst can be explained by coking reactions.

Deactivation by coking may be reflected in a coke deposit blocking all the active sites or accumulation of this deposit principally at the opening of the pores, thus blocking access to certain sites that are still vacant. The works of Mann (Catalysis Today 37 (1997) 331-349) give a good description of the interactions between the pore structure of catalysts, the deposits of coke in these structures and their effects on activity. These works showed in particular that the coke deposits can occupy a high proportion of the volume of the pores and thus begin to modify the structure and pore distribution of the catalyst. This modification may be reflected in more difficult access of the molecules to the catalytic sites or may even prevent access to certain sites, which greatly impacts the stability of the catalyst and often the selectivity. To limit this obstruction of the pores and leave as many sites as possible accessible, it is advisable to increase the pore volume, which takes place at the expense of the number of active sites and therefore the level of activity.

The works of Macho et al. (Applied Catalysis A: General 214 (2001) 251-257) relate to dehydration and simultaneous skeletal isomerization and isomerization of the position of the double bond, on C4 alcohols. In these works, gamma aluminas, optionally activated with acid, were used with various monohydric alcohols comprising an aliphatic chain with 4 carbons for evaluating their selectivity in terms of production of corresponding olefins and losses of other undesirable products such as methane, ethane, ethylene, propane, propylene, and C5+ products. It is thus demonstrated that an alumina functionalized with sulphuric acid is more active and more selective than a commercially available alumina for the proposed combined application, namely dehydration coupled with isomerization of the skeleton and of the position of the double bond of the resultant olefins. According to this document, it therefore seems that an alumina that is as acid as possible is necessary for combined dehydration and isomerization of C4 monohydric alcohols.

The present invention proposes to provide a method of producing C4 alkenes, starting from C4 monohydric alcohols, in which the cycle time, as well as the activity over time of the catalyst used, are improved relative to the alumina-based catalysts of the prior art.

AIM AND ADVANTAGES OF THE INVENTION

The present invention relates to a method of producing C4 olefins, from a feed of C4 monohydric alcohol, in which a reaction of dehydration of the monohydric alcohol to at least one olefin, and a reaction of skeletal isomerization of at least one of the olefins produced in one and the same reaction vessel, are carried out in the presence of an alumina-based catalyst with adapted porosity.

The alcohol is dehydrated and the olefin(s) produced is (are) isomerized. Skeletal isomerization is a reaction that is far quicker than the dehydration reaction, and consequently it is not generally possible to stop at the dehydration reaction.

The method according to the invention offers the advantage of improving the catalyst cycle time, owing to the pore distribution with a high level of open macroporosity. The activity of the catalyst over time is thus improved. This effect is probably due to the increase in volume offered to the catalytic coke, while minimizing the loss over time of active sites available for the reaction.

It should be noted that the increase in volume offered to the catalytic coke takes place at the expense of the number of active sites of the alumina, but does not cause an appreciable drop in activity, which is surprising in view of the existing teachings on this subject. Thus a catalyst is obtained which is more open in a well-targeted range of a catalyst that is active and capable of long durability in application.

DETAILED DESCRIPTION OF THE INVENTION

The present invention relates to a method of producing C4 olefins, by passing a feed of C4 monohydric alcohol over a catalyst, in which a reaction of dehydration of the monohydric alcohol to at least one olefin, and a reaction of skeletal isomerization of at least one of the olefins produced in one and the same reaction vessel, are carried out, said method being characterized in that the reactions of dehydration and of isomerization are effected in the presence of the catalyst, optionally containing a promoter, said catalyst being based on alumina, free from halogens and having a pore distribution such that the volume of pores with diameter greater than 0.1 µm measured by mercury porosimetry according to standard ASTM D4284-83 is comprised between 10 mL/100 g and 30 mL/100 g.

According to the present invention, the dehydration of the C4 monohydric alcohols and the is reaction of skeletal isomerization of the alkene obtained after dehydration, are catalysed by the same catalyst, on sites of the same nature.

The catalyst employed in the method according to the present invention has the characteristic feature that it has an adapted macropore volume. The adaptation of this volume is effected by usual treatments known to a person skilled in the art, among which may be mentioned addition of an organic pore-forming agent of polymer or non-polymer origin (compatible with its destruction during final calcination of the solid), steam ageing, autoclaving, chemical attack followed by washing, precoking.

The catalyst used in the method according to the invention is in the form of spheroids. This type of shape, once placed in the reactors, offers the advantage of being discharged easily, without forming plugs, even once the catalyst is coked. It also offers the advantage of ensuring homogeneous charging, in contrast to solids in the form of extrudates, as well as greater mechanical resistance to crushing.

The catalyst of spheroidal shape has a dual porosity, measured by mercury porosimetry. Analysis by mercury porosimetry corresponds to the intrusion of a volume of mercury characteristic of the existence of mesopores and macropores in said catalyst according to standard ASTM D4284-83 at a maximum pressure of 4000 bar, using a surface tension of 484 dyn/cm and a contact angle of 140° (value chosen following the recommendations of the work "Technique de l'ingénieur, traité analyse et caractérisation", page 1050, written by J. Charpin and B. Rasneur), it being assumed that the pores are of cylindrical shape. This technique provides the value of the mesoporous mercury volume, defined as being the mercury volume adsorbed by all of the pores having a diameter in the mesopore range, namely comprised between 3.6 and 100 nm. Similarly, the macroporous mercury volume is defined as being the mercury volume adsorbed by all of the pores having a diameter greater than 100 nm.

The dual porosity of the catalyst used in the method according to the present invention is characterized as follows: a macroporosity characterized by a macroporous mercury volume in a range of from 0.10 to 0.30 ml/g and preferably in a range of from 0.12 to 0.25 ml/g and a mesoporosity characterized by a mesoporous mercury volume in a range of from 0.25 to 0.7 ml/g, preferably in a range of from 0.34 to 0.48 ml/g. The macroporosity is also characterized by the presence of macroporous domains beyond 100 nm and/or results from an intraparticle textural macroporosity, the mesoporosity is also characterized by the presence of mesoporous domains in a range of from 7 to 50 nm and preferably in a range of from 8 to 10 nm. The proportion of the pore volume that is accessible (not occluded) of said spheroids having a pore size smaller than 20 nm is comprised between 60 and 75%.

The catalyst used in the method according to the present invention has a total pore volume defined by the aforementioned mercury porosity analysis comprised between 0.45 and 0.9 ml/g.

The catalyst is prepared according to techniques known to a person skilled in the art. First, alumina having the macroporosity according to the invention is prepared, using a pore-forming agent, optionally a pore opening technique, and finally calcination in air at a temperature above 550° C. The promoter is added to the alumina for forming or else is impregnated after forming.

Preferably, the solid catalyst is formed by one of the techniques known to a person skilled in the art, consisting of the technique of coagulation in drops (also known as the "oil drop" method) or the technique using granulation (bowl granulation).

The morphology and size distribution of the beads thus obtained are established by analysis of photographs obtained by scanning electron microscopy (SEM) and by image analysis (camera, determination of sphericity).

The catalyst according to the invention is in the form of spheroids, which preferably have an average diameter comprised between 1 and 2.5 mm. The term "average diameter" denotes the maximum diameter of a circle circumscribing the whole bead, whether it is ovoid or spherical.

The catalyst has a specific surface area $S_{BET}$ comprised between 180 and 270 m$^2$/g.

The catalyst employed in the present invention is based on alumina and comprises at least 50 wt. % of alumina, and generally at least 50 wt. % of gamma alumina, preferably at least 65 wt. %, and even more preferably at least 80 wt. %.

It can optionally further comprise up to 35 wt. %, and preferably at most 20 wt. %, and even more preferably between 0.1 and 35 wt. % or between 0.1 and 20 wt. % of another metal oxide, structured or unstructured. Preferably, said other oxide is a zeolite, for example ZSM-5.

The use of spheroids with diameter controlled to a small diameter makes it possible, moreover, to maximize the effect observed, through maximum development of the surface area offered to the catalytic coke.

At least one promoter can be added to the catalyst, making it possible to adjust the isomerization activity of the catalyst.

The promoter is selected from the metals of groups 4 (Ti, Zr, Hf), 5 (V, Nb, Ta), 6 (Cr, Mo, W) and/or 12 (Zr, Cd, Hg) or oxides of alkali metals (Na, K).

The presence of a promoter from groups 4, 5, 6 and/or 12, optionally combined with an increase in the reaction temperature (preferably a temperature of at least 480° C. and of at most 600° C. or 570° C.), makes it possible to increase the degree of skeletal isomerization, whereas the presence of an alkali metal promoter, selected from potassium and/or sodium, provides little orientation towards the reaction of skeletal isomerization.

When the promoter is an element from groups 4, 5, 6 and/or 12, the quantity of promoter added to the catalyst is preferably at least 0.1 wt. % (calculated as oxide) and at most 1 wt. % relative to the catalyst.

Most often, the promoter is Ti, V, W. Preferably, the promoter is Ti.

A preferred catalyst is constituted by alumina and oxide of the promoter(s), preferably the promoter is Ti, V, W, and it is preferably titanium oxide.

When the promoter is sodium or potassium (preferably in the form of oxide), the quantity of promoter added to the catalyst is at least 0.1 wt. % and at most 2 wt. % (calculated as oxide). A preferred catalyst is constituted by alumina and oxide of the promoter(s).

The catalyst, after calcination, does not contain halogen.

The C4 monohydric alcohol contained in the feed can be from various sources: in particular it can have been produced by a biological route or by a chemical route.

The n-butanol can thus be obtained by acetone-butyl fermentation of glucose, as described in FR-B1-2 634 218. Patent application US 2009/226991, which describes the production of isobutanol by a biological route, may also be mentioned.

The alcohol can also be produced by a method of transformation by a chemical route.

The C4 monohydric alcohol can be obtained from syngas or by direct or indirect hydration of olefins, or by oxo synthesis. The hydration of olefins to obtain alcohols, including C4 alcohols, is described in detail in "Techniques de l'ingénieur, Opérations unitaires. Génie de la réaction chimique", Reference J5550, Date of publication: 10 Mar. 1997, Bernard TORCK. Reference is also made to the work "Procédés de pétrochimie: Les grands intermédiaires oxygénés, chlorés et nitrés" by Alain Chauvel, Gilles Lefebvre, L. Castex, Pierre Leprince, Ecole nationale supérieure du pétrole et des moteurs (France). Centre d'études supérieures de raffinage et de génie chimique.

The C4 monohydric alcohol used in the method is selected from 1-butanol, 2-butanol, isobutanol, tert-butanol, alone or mixed.

Very preferably, the C4 alcohol is isobutanol.

The feed containing the C4 monohydric alcohol can comprise up to 50 wt. % of water, as well as the impurities associated with the production process (mainly nitrogen, acids, aldehydes, non-C4 alcohols).

Moreover, the presence of water in the process, whether it is introduced with the alcohol or it results from the reaction of dehydration of the alcohol, advantageously makes it possible to limit the oligomerization reactions, which are inevitable during the reaction of skeletal isomerization.

The method according to the present invention is carried out at a temperature comprised between 250 and 600° C., preferably between 330 and 570° C., at a pressure comprised between 0.1 and 1 MPa, preferably between 0.1 and 0.5 MPa, with an hourly space velocity (volume of feed per volume of catalyst per hour) comprised between 0.1 and 10 h$^{-1}$, preferably between 0.8 and 1.5 h$^{-1}$.

The reaction unit provided with the catalyst in the form of spheroids used for carrying out the method according to the present invention operates either with a fixed bed or with a moving bed, preferably with a fixed bed. When it operates with a fixed bed or with a moving bed, the catalyst is regenerated periodically and said unit alternately performs the reaction for production of C4 alkenes and the regeneration of said catalyst so as to remove the coke deposited on its surface during the reactions. According to an alternative use, with a moving bed, the catalyst can be transported between the reaction zone and the regeneration zone.

EXAMPLES

Example 1

Catalyst Synthesis

Synthesis is carried out by bowl granulation from powdered alumina in a rotating pan. The coated particles are dried and calcined in air in a manner suitable for obtaining a gamma alumina. Catalyst A is obtained in this way. It is this type of catalyst (activated alumina of grade A) that is often used in the documents of the prior art. The reference catalyst is obtained from the company Axens, and is listed in their catalogue under the names AA 2/5 Grade A.

It is a catalyst of spherical shape, having a diameter comprised between 2 and 5 nm (see Table 1 below).

A post-treatment with steam, extraction with water, drying and calcination is used for creating wider pores from catalyst A in order to obtain catalysts B and C, at the expense of a slight loss of surface area. Moreover, sieving is used, so that only the catalyst fraction of smaller diameter is removed. Between catalysts B and C, the severity of the treatment of hydrothermal ageing is varied, and the washing steps are also adjusted.

A solid organic precursor (polymer microbeads) is used during the bowl granulation of the powdered alumina, before using the same steps as for catalyst C. In this way, catalyst D is obtained, of which the volume of pores with diameter greater than 0.1 µm is 33 mL/100 g and therefore is not according to the invention.

Catalyst E is obtained starting from catalyst C by adding, before the hydrothermal treatment, a step of dry impregnation with sodium hydroxide solution.

Catalyst F is obtained by an Oil Drop technique from an alumina gel, in which $TiO_2$ was added. An organic pore-forming agent was also used (isoparaffin hydrocarbon). The final calcination is adjusted to obtain a targeted macroporosity.

The following table shows the characteristics of the catalysts obtained.

TABLE 1

|  | A (comparative) | B | C | D (comparative) | E | F |
|---|---|---|---|---|---|---|
| $V_{>0.1 \mu m}$ (mL/100 g) | 3 | 15 | 20 | 33 | 21 | 17 |
| Surface area (m$^2$/g) | 335 | 270 | 195 | 142 | 187 | 201 |
| $V_{porous\ total}$ (mL/100 g) | 37 | 54 | 68 | 104 | 69 | 65 |
| Average diameter (mm) | 3.5 | 2.8 | 2.5 | 2.3 | 2.5 | 2.0 |
| $V_{meso}$ (mL/100 g) | 34 | 39 | 48 | 71 | 48 | 48 |
| Promoter | — | — | — | — | Na$_2$O 1% | TiO$_2$ 0.5% |

Example 2

Activity in Dehydration of 1-butanol

Each catalyst is tested for about 500 h in an identical manner in order to compare their performance in terms of service life and activity. 75 g of catalyst is used, diluted in order to have a thermal profile that is as isothermal as possible, as the reaction under investigation is highly endothermic.

Before the test proper, the solid is activated at 550° C. in air for 2 hours. This activation consists of calcination, which aims to burn off any traces of oil and grease, and to dry the catalyst before it is used.

75 g/h of commercial pure 1-butanol with addition of 7% of distilled water is injected onto this catalyst. At the reactor outlet, the gaseous phase, organic liquid phase and aqueous liquid phase are separated. No recycling is used. The reaction conditions employed are: a temperature of 380° C., the reactor being isothermal, and a pressure of 0.5 bar relative.

The analyses of the aqueous phases and gaseous organic phases indicate the nature of the compounds formed. Presence of liquid organic phase to be separated from the aqueous phase was not observed in any of the tests.

The hydrocarbon part of the gaseous phase contains predominantly butenes from propylene and pentenes, as well as traces of C1, C2, C3, C5 and C6 hydrocarbons and small quantities of CO, $CO_2$ and hydrogen.

The aqueous phase also contains other oxygen-containing derivatives (ethers and ketones, mainly dibutyl ether) but quantification of these species was not undertaken. Only water was recorded, and the level of compounds not converted to hydrocarbon is included under the heading "alcohol".

The conversion to alcohol is monitored by titrating the alcohol present in the aqueous phase leaving the unit. Conversely, the mass of aqueous phase is recalculated from the conversion in order to normalize the material balance to 100.

The results obtained with the reference catalyst according to the prior art are given in Table 2.

TABLE 2

(comparative)

| | | effluent Time in use | | | |
|---|---|---|---|---|---|
| Cat. A | Feed | 1 h | 30 h | 150 h | 350 h |
| Methane | | 0.09 | 0.09 | 0.08 | 0.07 |
| Ethane | | 0.02 | 0.01 | 0.03 | 0.02 |
| Ethylene | | 0.29 | 0.13 | 0.12 | 0.09 |
| Propane | | 0.00 | 0.00 | 0.00 | 0.00 |
| Propylene | | 0.61 | 0.29 | 0.27 | 0.23 |
| n-Butane | | 0.02 | 0.02 | 0.02 | 0.01 |
| Trans-2-butene | | 13.64 | 14.39 | 18.32 | 14.83 |
| 1-butene | | 31.47 | 35.01 | 43.79 | 39.04 |
| Isobutene | | 1.04 | 0.77 | 0.00 | 0.00 |
| Cis-2-butene | | 19.41 | 14.66 | 1.35 | 1.12 |
| Total C5 | | 1.88 | 1.58 | 0.86 | 0.13 |
| Total C6 | | 1.08 | 0.91 | 0.52 | 0.08 |
| Total C6+ | | 0.17 | 0.14 | 0.07 | 0.01 |
| Water (recalc.) | 5 | 27.4 | 27.0 | 26.0 | 22.8 |
| Alcohol | 95 | 3 | 5 | 9 | 22 |
| Total | 100 | 100 | 100 | 100 | 100 |
| Conversion | | 97 | 95 | 91 | 77 |
| Selectivity for 1-butene | | 45 | 51 | 67 | 71 |
| Selectivity for butene | | 94 | 95 | 97 | 100 |

The tests carried out according to the method of the invention employing catalysts B to E are shown respectively in the following Tables 3 to 6:

TABLE 3

| | | effluent Time in use | | | |
|---|---|---|---|---|---|
| Cat. B | Feed | 1 h | 30 h | 150 h | 350 h |
| Methane | | 0.09 | 0.09 | 0.08 | 0.07 |
| Ethane | | 0.02 | 0.01 | 0.03 | 0.02 |
| Ethylene | | 0.27 | 0.13 | 0.12 | 0.09 |
| Propane | | 0.00 | 0.00 | 0.00 | 0.00 |
| Propylene | | 0.67 | 0.29 | 0.27 | 0.23 |
| n-Butane | | 0.02 | 0.02 | 0.02 | 0.01 |
| Trans-2-butene | | 13.20 | 18.15 | 18.04 | 17.07 |
| 1-butene | | 42.74 | 43.21 | 46.75 | 47.20 |
| Isobutene | | 6.38 | 3.32 | 0.67 | 0.00 |
| Cis-2-butene | | 1.47 | 1.80 | 1.33 | 1.29 |
| Total C5 | | 2.27 | 1.17 | 0.62 | 0.23 |
| Total C6 | | 1.30 | 0.68 | 0.38 | 0.13 |
| Total C6+ | | 0.21 | 0.10 | 0.05 | 0.02 |
| Water (recalc.) | 4.3 | 26.4 | 26.5 | 26.2 | 25.6 |
| Alcohol | 95.7 | 5 | 4 | 6 | 8 |
| Total | 100 | 100 | 100 | 100 | 100 |
| Conversion | | 95 | 95 | 94 | 91 |
| Selectivity for 1-butene | | 62 | 63 | 69 | 71 |
| Selectivity for butene | | 93 | 97 | 98 | 99 |

TABLE 4

| | | effluent Time in use | | | |
|---|---|---|---|---|---|
| Cat. C | Feed | 1 h | 30 h | 150 h | 350 h |
| Methane | | 0.09 | 0.09 | 0.08 | 0.07 |
| Ethane | | 0.02 | 0.01 | 0.03 | 0.02 |
| Ethylene | | 0.19 | 0.13 | 0.12 | 0.09 |
| Propane | | 0.00 | 0.00 | 0.00 | 0.00 |
| Propylene | | 0.55 | 0.29 | 0.27 | 0.23 |
| n-Butane | | 0.02 | 0.02 | 0.02 | 0.01 |
| Trans-2-butene | | 12.61 | 13.53 | 14.18 | 15.57 |
| 1-butene | | 44.72 | 46.68 | 48.70 | 48.68 |
| Isobutene | | 4.41 | 2.56 | 0.65 | 0.00 |
| Cis-2-butene | | 1.25 | 1.18 | 1.40 | 1.54 |
| Total C5 | | 1.88 | 1.62 | 0.91 | 0.16 |
| Total C6 | | 1.08 | 0.94 | 0.55 | 0.09 |
| Total C6+ | | 0.17 | 0.14 | 0.08 | 0.01 |
| Water (recalc.) | 5 | 26.5 | 26.7 | 26.5 | 26.3 |
| Alcohol | 95 | 6 | 6 | 7 | 8 |
| Total | 100 | 100 | 100 | 100 | 100 |
| Conversion | | 93 | 94 | 93 | 92 |
| Selectivity for 1-butene | | 67 | 69 | 73 | 74 |
| Selectivity for butene | | 94 | 95 | 97 | 100 |

TABLE 5

(comparative)

| | | effluent Time in use | | | |
|---|---|---|---|---|---|
| Cat. D | Feed | 1 h | 30 h | 150 h | 350 h |
| Methane | | 0.09 | 0.07 | 0.08 | 0.07 |
| Ethane | | 0.02 | 0.01 | 0.03 | 0.02 |
| Ethylene | | 0.11 | 0.10 | 0.03 | 0.00 |
| Propane | | 0.00 | 0.00 | 0.00 | 0.00 |
| Propylene | | 0.24 | 0.22 | 0.07 | 0.01 |
| n-Butane | | 0.02 | 0.02 | 0.02 | 0.01 |
| Trans-2-butene | | 11.38 | 10.88 | 7.01 | 6.39 |
| 1-butene | | 40.05 | 41.77 | 41.40 | 36.25 |

TABLE 5-continued (comparative)

| Cat. D | Feed | effluent Time in use | | | |
|---|---|---|---|---|---|
| | | 1 h | 30 h | 150 h | 350 h |
| Isobutene | | 0.85 | 0.65 | 0.00 | 0.00 |
| Cis-2-butene | | 1.13 | 0.95 | 4.67 | 4.44 |
| Total C5 | | 0.74 | 0.71 | 0.23 | 0.02 |
| Total C6 | | 0.43 | 0.41 | 0.14 | 0.01 |
| Total C6+ | | 0.07 | 0.06 | 0.02 | 0.00 |
| Water (recalc.) | 4.5 | 22.1 | 22.3 | 21.6 | 19.5 |
| Alcohol | 95 | 23 | 22 | 25 | 33 |
| Total | 100 | 100 | 100 | 100 | 100 |
| Conversion | | 76 | 77 | 74 | 65 |
| Selectivity for 1-butene | | 73 | 75 | 77 | 77 |
| Selectivity for butene | | 97 | 97 | 99 | 100 |

TABLE 6

| Cat. E | Feed | effluent Time in use | | | |
|---|---|---|---|---|---|
| | | 1 h | 30 h | 150 h | 350 h |
| Methane | | 0.09 | 0.09 | 0.08 | 0.07 |
| Ethane | | 0.02 | 0.01 | 0.03 | 0.02 |
| Ethylene | | 0.08 | 0.07 | 0.04 | 0.01 |
| Propane | | 0.00 | 0.00 | 0.00 | 0.00 |
| Propylene | | 0.16 | 0.15 | 0.09 | 0.02 |
| n-Butane | | 0.02 | 0.02 | 0.02 | 0.01 |
| Trans-2-butene | | 2.58 | 3.12 | 2.49 | 1.64 |
| 1-butene | | 51.07 | 52.56 | 53.36 | 53.63 |
| Isobutene | | 0.00 | 0.00 | 0.00 | 0.00 |
| Cis-2-butene | | 1.87 | 2.08 | 1.53 | 1.19 |
| Total C5 | | 0.50 | 0.47 | 0.30 | 0.08 |
| Total C6 | | 0.29 | 0.27 | 0.18 | 0.05 |
| Total C6+ | | 0.05 | 0.04 | 0.03 | 0.01 |
| Water (recalc.) | 4.5 | 22.6 | 23.3 | 23.0 | 22.6 |
| Alcohol | 95 | 21 | 18 | 19 | 21 |
| Total | 100 | 100 | 100 | 100 | 100 |
| Conversion | | 78 | 81 | 80 | 78 |
| Selectivity for 1-butene | | 90 | 89 | 92 | 95 |
| Selectivity for butene | | 98 | 98 | 99 | 100 |

According to these results, it is noted that:
- the service life of the catalyst is increased by the presence of a high level of macroporosity: the drop in activity is less after a cycle time of 350 h, which makes it possible to envisage a longer cycle for the catalysts employed in the method according to the present invention;
- the selectivity for the sought alcohol (1-butene for 1-butanol, isobutene for isobutanol) is increased by the addition of a promoter ($Na_2O$) as well as by the decrease in external surface area,
- the reduction of initial activity is largely compensated for by the gain in stability, as the residual activity beyond 350 h is greater.

Example 3

Activity in Dehydration of 1-butanol with Skeletal Isomerization

Each catalyst is tested for about 100 h in an identical manner in order to compare their performance in terms of service life and activity. 75 g of catalyst is used, diluted in order to have a thermal profile that is as isothermal as possible, as the reaction under investigation is highly endothermic.

Before the test proper, the solid was activated at 550° C. in air for 2 h. This activation consists of calcination, which aims to burn off any traces of oil and grease, and to dry the catalyst before it is used.

75 g/h of commercial pure 1-butanol with addition of distilled water is injected onto this catalyst. At the reactor outlet, the gaseous phase, organic liquid phase and aqueous liquid phase are separated. No recycling is used. The reaction conditions employed are: a temperature of 480° C., the reactor being isothermal, and a pressure of 0.5 bar relative.

The analyses of the aqueous phases and gaseous organic phases indicate the nature of the compounds formed. Presence of liquid organic phase to be separated from the aqueous phase was not observed in any of the tests.

The hydrocarbon part of the gaseous phase contains predominantly butenes from propylene and butenes, as well as traces of C1, C2, C3, C5 and C6 hydrocarbons and small quantities of CO, $CO_2$ and hydrogen.

The aqueous phase also contains other oxygen-containing derivatives (ethers and ketones, mainly dibutyl ether) but quantification of this species was not undertaken. Only water was recorded, and the level of compounds not converted to hydrocarbon is included under the heading "alcohol".

TABLE 7

| Cat. A: sk isom | Feed | effluent Time in use | | | |
|---|---|---|---|---|---|
| | | 1 h | 30 h | 60 h | 100 h |
| Methane | | 0.14 | 0.16 | 0.15 | 0.16 |
| Ethane | | 0.04 | 0.02 | 0.05 | 0.05 |
| Ethylene | | 1.87 | 1.30 | 0.75 | 0.44 |
| Propane | | 0.11 | 0.10 | 0.07 | 0.02 |
| Propylene | | 3.47 | 2.11 | 1.45 | 0.92 |
| n-Butane | | 0.02 | 0.02 | 0.02 | 0.01 |
| Trans-2-butene | | 13.12 | 12.46 | 9.20 | 4.84 |
| 1-butene | | 5.87 | 5.18 | 3.40 | 2.27 |
| Isobutene | | 25.60 | 30.48 | 36.80 | 34.57 |
| Cis-2-butene | | 8.75 | 9.40 | 7.22 | 3.80 |
| Total C5 | | 6.10 | 4.24 | 3.74 | 2.72 |
| Total C6 | | 2.86 | 2.21 | 1.79 | 1.36 |
| Total C6+ | | 3.48 | 2.76 | 2.26 | 1.36 |
| Water (recalc.) | 5.1 | 28.1 | 27.8 | 26.6 | 22.0 |
| Alcohol (tert-butanol) | 95 | 0 | 2 | 6 | 25 |
| Total | 100 | 100 | 100 | 100 | 100 |
| Conversion | | 100 | 98 | 93 | 73 |
| Selectivity for 1-butene | | 8 | 7 | 5 | 4 |
| Selectivity for butene | | 75 | 82 | 85 | 87 |

TABLE 8

| Cat. G: sk isom | Feed | effluent Time in use | | | |
|---|---|---|---|---|---|
| | | 1 h | 30 h | 60 h | 100 h |
| Methane | | 0.17 | 0.20 | 0.16 | 0.17 |
| Ethane | | 0.05 | 0.06 | 0.05 | 0.06 |
| Ethylene | | 1.41 | 1.05 | 0.70 | 0.30 |
| Propane | | 0.07 | 0.05 | 0.05 | 0.03 |
| Propylene | | 2.12 | 1.64 | 1.20 | 0.57 |
| n-Butane | | 0.02 | 0.02 | 0.02 | 0.01 |
| Trans-2-butene | | 14.93 | 14.60 | 12.77 | 13.07 |

TABLE 8-continued

| Cat. G: sk isom | Feed | effluent Time in use | | | |
|---|---|---|---|---|---|
| | | 1 h | 30 h | 60 h | 100 h |
| 1-butene | | 6.36 | 6.04 | 5.56 | 4.36 |
| Isobutene | | 26.62 | 30.79 | 34.62 | 36.10 |
| Cis-2-butene | | 9.95 | 8.95 | 8.87 | 8.71 |
| Total C5 | | 5.12 | 4.01 | 2.90 | 1.38 |
| Total C6 | | 2.61 | 1.93 | 1.40 | 0.72 |
| Total C6+ | | 2.31 | 1.78 | 1.28 | 0.66 |
| Water (recalc.) | 4.5 | 27.4 | 27.2 | 26.7 | 25.6 |
| Alcohol (tert-butanol) | 95 | 1 | 2 | 4 | 8 |
| Total | 100 | 100 | 100 | 100 | 100 |
| Conversion | | 99 | 98 | 96 | 91 |
| Selectivity for 1-butene | | 9 | 9 | 8 | 7 |
| Selectivity for butene | | 81 | 85 | 89 | 95 |

Tables 8 and 9 above give the differences in catalytic activity between catalyst A, according to the prior art, and catalyst F, impregnated with Ti. It is noted that there is greater conversion of the feed alcohol after 100 h for catalyst F used in the method according to the invention. Moreover, the rate of recovery of C4 olefins (i.e. the selective recovery of olefins with 4 carbon atoms) is increased overall by the presence of the porosity profile of the catalyst used in the method according to the present invention.

The invention claimed is:

1. A method of producing C4 olefins, comprising passing a feed of C4 monohydric alcohol over a catalyst, dehydrating of the monohydric alcohol to at least one olefin, and skeletal isomerization of at least one of the olefins produced in one and the same reaction vessel, wherein the reactions of dehydration and of isomerization are carried out in the presence of the catalyst, optionally containing a promoter, said catalyst being based on alumina, free from halogens and having a pore distribution such that the volume of pores with diameter greater than 0.1 μm measured by mercury porosimetry according to standard ASTM D4284-83 is between 10 mL/100 g and 30 mL/100 g, and a total pore volume defined by analysis using mercury porosimetry between 0.45 and 0.9 ml/g wherein said catalyst has a surface area $S_{BET}$ between 180 and 270 m²/g.

2. The method according to claim 1, in which the catalyst comprises at least 50 wt. % of gamma alumina.

3. The method according to claim 1, in which said catalyst is in the form of spheroids.

4. The method according to claim 1, in which a promoter from metals of groups 4, 5, 6 and/or 12 is added to said catalyst.

5. The method according to claim 4, in which the promoter is Ti, V, or W.

6. The method according to claim 4, in which the quantity of promoter is at least 0.1 wt. % and at most 1 wt. % (calculated as oxide) relative to the catalyst.

7. The method according to claim 1, in which a promoter comprising potassium and/or sodium is added to said catalyst.

8. The method according to claim 7, in which the quantity of promoter is at least 0.1 wt. % and at most 2 wt. % (calculated as oxide) relative to the catalyst.

9. The method according to claim 1, in which the C4 monohydric alcohol contained in the feed is 1 butanol, 2-butanol, isobutanol, or tert-butanol, alone or mixed.

10. The method according to claim 1, in which the monohydric alcohol is isobutanol.

11. The method according to claim 1, in which said feed comprises up to 50 wt. % of water.

12. The method according to claim 1, carried out at a temperature between 250 and 600° C. at a pressure between 0.1 and 1 MPa, and with an hourly space velocity (volume of feed per volume of catalyst per hour) between 0.1 and 10 h⁻¹.

13. The method according to claim 3, wherein the spheroids have an average diameter comprised between 1 and 2.5 mm.

14. The method according to claim 12, wherein the temperature is 330 to 570° C., the pressure is 0.1 to 0.5 MPa, and the hourly space velocity is 0.8 to 1.5 h⁻¹.

* * * * *